(12) United States Patent
Tymczak et al.

(10) Patent No.: US 10,125,151 B2
(45) Date of Patent: Nov. 13, 2018

(54) METALLOBORANES FOR HIGH DENSITY HYDROGEN STORAGE

(71) Applicants: Christopher John Tymczak, Humble, TX (US); Alireza Akbarzadeh, Spring, TX (US); Daniel Vrinceanu, Pearland, TX (US)

(72) Inventors: Christopher John Tymczak, Humble, TX (US); Alireza Akbarzadeh, Spring, TX (US); Daniel Vrinceanu, Pearland, TX (US)

(73) Assignee: Texas Southern University, Houston, TX (US)

( * ) Notice: Subject to any disclaimer, the term of this patent is extended or adjusted under 35 U.S.C. 154(b) by 7 days.

(21) Appl. No.: 15/421,987

(22) Filed: Feb. 1, 2017

(65) Prior Publication Data
US 2017/0145036 A1    May 25, 2017

Related U.S. Application Data (63) Continuation of application No. PCT/US2015/043443, filed on Aug. 3, 2015.
(Continued)

(51) Int. Cl.
*B01J 20/02* (2006.01)
*B01J 20/04* (2006.01)
(Continued)

(52) U.S. Cl.
CPC .......... *C07F 5/022* (2013.01); *B01J 20/0211* (2013.01); *B01J 20/0248* (2013.01); *B01J 20/04* (2013.01);
(Continued)

(58) Field of Classification Search
CPC ..... C01B 3/0026; C01B 3/001; C01B 3/0031; C01B 3/0015; C01B 3/04; C01B 35/04;
(Continued)

(56) References Cited

U.S. PATENT DOCUMENTS

2009/0098423 A1* 4/2009 Bhattacharjee ......... C01B 3/001
429/498

FOREIGN PATENT DOCUMENTS

GB    1071376 A  *  6/1967  ............... C01B 6/00
WO    2009051940 A1    4/2009

OTHER PUBLICATIONS

Alireza Akbarzadeh et al. High density H2 associative absorption on Titanium alphaborozene (Ti2B6H6): An ab-initio case study. APS March Meeting Abstracts, 2011, v. 1, p. 1081, abstract.*
(Continued)

*Primary Examiner* — Amber R Orlando
*Assistant Examiner* — Syed T Iqbal
(74) *Attorney, Agent, or Firm* — Benjamin Aaron Adler (57) ABSTRACT

Provided herein are the metalloborane compounds, MOF-metalloborane compositions, and hydrogen storage system used for high density hydrogen storage. The compounds and compositions may have the structure $M_2B_6H_6$ or MOF-$M_2B_6H_6$-dicarboxylic acid. Particularly the transition metal M may be titanium or scandium and the MOF may be MOF5. The hydrogen storage systems hydrogen absorbed to the metalloborane compounds or to the MOF-metalloborane compositions. Methods of storing hydrogen are provided comprising flowing or passing hydrogen gas for absorptive contact with the metalloborane compounds or to the MOF-metalloborane compositions. Also provided is a method for calculating the hydrogen storage capacity of a metalloborane is provided in which random sampling of the thermodynamic states of a two-system model of hydrogen in the
(Continued)

presence of a metal organic framework-metalloborane crystal structure is used to calculate probability of hydrogen absorption.

19 Claims, 6 Drawing Sheets

Related U.S. Application Data (60) Provisional application No. 62/031,993, filed on Aug. 1, 2014.

(51) Int. Cl.
    *B01J 20/22* (2006.01)
    *C01B 3/00* (2006.01)
    *C01B 35/04* (2006.01)
    *C07F 5/02* (2006.01)
    *C07F 7/28* (2006.01)
    *C07F 5/00* (2006.01)
    *C07F 5/06* (2006.01)
    *C01B 3/04* (2006.01)

(52) U.S. Cl.
    CPC .............. *B01J 20/226* (2013.01); *C01B 3/001* (2013.01); *C01B 3/0015* (2013.01); *C01B 3/0026* (2013.01); *C01B 3/04* (2013.01); *C01B 35/04* (2013.01); *C07F 5/003* (2013.01); *C07F 5/069* (2013.01); *C07F 7/28* (2013.01); *Y02E 60/328* (2013.01)

(58) Field of Classification Search
    CPC ...... Y02E 60/327; Y02E 60/328; H01M 8/00; B01J 20/0211; B01J 20/0248; B01J 20/04; B01J 20/226; C07F 5/003; C07F 5/022; C07F 5/069; C07F 7/28
    See application file for complete search history.

(56) References Cited

OTHER PUBLICATIONS

Yan et al. "Ruthenacarboranes from the Reaction of nido-1,2-(Cp*RuH)2B3H7 with HCtCCO2Me, Cp* ) è5-C5Me5. Hydrometalation, Alkyne Incorporation, and Functional Group Modification via Cooperative Metal-Boron Interactions within a Metallaborane Cluster Framework" J. Am. Chem. Soc. 2003, 125, 16367-16382.*

Alireza Akbarzadeh, C.J. Tymzcak, 2011 High density H2 associative absorption on Titanium alpha-borozene (Ti2B6H6): An ab-initio case study, APS March Meeting 2011 vol. 56, No. 1 p. 1081 (Abstract ID: BAPS.2011.Mar.K1.81).

* cited by examiner

METALLOBORANES FOR HIGH DENSITY HYDROGEN STORAGE

CROSS-REFERENCE TO RELATED APPLICATIONS

This application is a continuation under 35 U.S.C. § 120 of pending international application PCT/US2015/043443, filed Aug. 3, 2015, which claims benefit of priority under 35 U.S.C. § 119(e) of provisional application U.S. Ser. No. 62/031,993, filed Aug. 1, 2014, the entirety of both of which are hereby incorporated by reference.

BACKGROUND OF THE INVENTION

Field of the Invention

The present invention relates to the field of hydrogen storage. More specifically, the present invention relates to metalloboranes embedded in metal organic frameworks for high-density hydrogen absorption and storage.

Description of the Related Art

Due to the growing concern on fossil fuel depletion and global warming caused by burning fossil fuels, it is imperative to search for alternative energy systems. Hydrogen is a clean energy carrier and has been considered as one of the most promising substitutes for fossil fuels.

To use hydrogen fuel at the fullest capacity, however, an optimal method to store and release hydrogen with minimum energy cost is required. Generally, an efficient hydrogen storage method has to meet three criteria, (1) high gravimetric density; (2) optimal thermodynamics properties, i.e., hydrogen bonding to a material should be neither too strong nor too weak; and (3) optimal reaction kinetics for uptake and release of hydrogen with low energy cost.

Among the most commonly used methods of storing hydrogen, molecular adsorption and solid-state storage are considered best for the purpose of on-board applications in the transportation sector. However, despite extensive study, a highly efficient method for hydrogen storage remains elusive due to the difficulty to meet all three of the criteria described above. For example, metal hydrides, one of the most commonly used hydrogen storage material, often exhibits metal-H binding that is too strong for hydrogen release, whereas the weak physisorption between hydrogen and graphite nano-structured material often requires storage at cryogenic temperature to prevent hydrogen emitting. To date, the best commercial hydrogen storage media can only store up to 4% hydrogen per weight of storage media at room temperatures and 8% at cryogenic temperatures at 100 bar.

Yildrin et al. proposed that a Kubas-type interaction, which is an interaction between the d-orbital of transition metals and the sigma bonding of the hydrogen molecule, could effectively mediate the hydrogen uptake since the binding strength of Kubas-type interaction is between the chemisorption and physisorption, resulting in reversible absorption and release of hydrogen at ambient temperature. Yildrin et al. is able to use titanium decorated carbon nanotubes for hydrogen storage. However, the transition metal atoms tend to coalesce into an island when attached to nanostructures, thus destroying the storage capacity. Recently, Singh et al. conducted first principles study on metallocarborane decorated by the transition metals scandium and titanium. The simulation results of Singh et al. determined that d-orbital's of these metals can absorb hydrogen with binding energy of ~30 kJ/mol, which is in the range necessary to meet the second criterion. Moreover, transition metals do not aggregate on the metallocarborane, which is an advantage over carbon nanostructures. These authors also found that the binding between hydrogen and the metallocarborane is due to Kubas interactions.

Thus, there is a recognized need for an improved compounds, compositions, systems and methods for storage of hydrogen gas. The present invention fulfill this longstanding need and desire in the art.

SUMMARY OF THE INVENTION

The present invention is directed to a metalloborane compound having a chemical structure $M_2B_6H_6$ where M is a transition metal.

The present invention also is directed to method for storing hydrogen. The method comprises flowing hydrogen gas for absorptive contact with the metalloborane described herein such that the hydrogen molecules bind thereto. The present invention is directed to a related method further comprising releasing the stored hydrogen to power a vehicle.

The present invention is direct further to a molecular hydrogen storage system. The storage system comprises the metalloborane compound described herein and one or more hydrogen's absorbed to the metalloborane.

The present invention is direct further still to a hydrogen storage composition. The composition comprises a metalloborane compound linked to a metal organic framework.

The present invention is directed further still to a method for storing hydrogen. The method comprises flowing hydrogen gas for absorptive contact with the hydrogen storage composition described herein such that the hydrogen molecules bind to the metalloborane. The present invention is directed to a related method further comprising releasing the stored hydrogen to power a vehicle.

The present invention is direct further still to a molecular hydrogen storage system. The storage system comprises the hydrogen storage composition described herein and one or more hydrogen's absorbed to the metalloborane comprising the composition.

The present invention is direct further still to a method for calculating the hydrogen storage capacity of a metalloborane. The method comprises synthesizing a metal organic framework-metalloborane crystal structure and calculating the lattice data for the crystal structure. The lattice data is input into a two-system model of hydrogen and the thermodynamic states of the first and second systems is sampled. A probability of hydrogen molecules moving to a random open binding site on the metalloborane is calculated, where the probability correlates to the hydrogen storage capacity of the metalloborane.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 4A-4C shows the results of density of states (DOS) for compounds described herein. FIG. 4A shows the density of states for $Sc_2B_6H_6$. FIG. 4B shows the density of states for $Sc_2B_6H_6$-$(1,0)H_2$

DETAILED DESCRIPTION OF THE INVENTION

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

In one embodiment of the present invention there is provided metalloborane compound having a chemical structure: $M_2B_6H_6$ where M is a transition metal. In aspects of this embodiment the structure may be $Ti_2B_6H_6$ or $Sc_2B_6H_6$. In this embodiment the metalloborane may be linked to a metal organic framework (MOF). In an aspect thereof the metal organic framework may be an MOF5 comprising a $M_2B_6H_6$-dicarboxylic acid. A representative example of the MOF5 structure is MOF5-$M_2B_6H_6$—$(COOH)_2$.

In another embodiment of the present invention there is provided a method for storing hydrogen, comprising the step of flowing hydrogen gas for absorptive contact with the metalloborane as described supra whereby hydrogen molecules bind thereto. In this embodiment the stored hydrogen may comprise a structural configuration of $M_2B_6H_6$-$(n,m)$ $H_2$ wherein n and m are independently 0 to 6. Particularly, the metal M may be titanium or scandium. Further to this embodiment the method may comprise releasing the stored hydrogen to power a vehicle.

In yet another embodiment of the present invention there is provided a molecular hydrogen storage system, comprising the metalloborane compound as described supra; and one or more hydrogens absorbed to the metalloborane. In this embodiment the hydrogen may be absorbed via Kubas interaction and van der Waals interaction. Also, the structural configuration of the molecular storage system may be $M_2B_6H_6$-$(n,m)H_2$ configuration wherein n and m are independently 0 to 6.

In yet another embodiment of the present invention there is provided a hydrogen storage composition, comprising a metalloborane compound linked to a metal organic framework. In this embodiment the metalloborane compound may be $M_2B_6H_6$ wherein M is a transition metal. Also the metal organic framework may be an MOF5 comprising $M_2B_6H_6$—$(COOH)_2$. In aspects of this embodiment the metal organic framework may be an MOF5 comprising $Ti_2B_6H_6$—$(COOH)_2$ or an MOF5 comprising $Sc_2B_6H_6$—$(COOH)_2$.

In yet another embodiment of the present invention there is provided a method for storing hydrogen, comprising the step of flowing hydrogen gas for absorptive contact with the hydrogen storage composition described supra whereby hydrogen molecules bind to the metalloborane. In this embodiment the stored hydrogen may comprise a structural configuration of $M_2B_6H_6$-$(n,m)H_2$ wherein n and m are independently 0 to 6. Particularly, the metal M may be titanium or scandium. Further to this embodiment the method may comprise releasing the stored hydrogen to power a vehicle.

In yet another embodiment of the present invention there is provided a molecular hydrogen storage system, comprising the hydrogen storage composition as described supra; and one or more hydrogens absorbed to the metalloborane comprising the composition. In this embodiment the hydrogen may be absorbed via Kubas interaction and van der Waals interaction. Also, the structural configuration of the molecular storage system may be $M_2B_6H_6$-$(n,m)H_2$ configuration wherein n and m are independently 0 to 6.

In yet another embodiment of the present invention there is provided a method for calculating the hydrogen storage capacity of a metalloborane, comprising the steps of synthesizing a metal organic framework-metalloborane crystal structure; calculating lattice data for the crystal structure; inputting the lattice data into a two-system model of hydrogen; sampling the thermodynamic states of the first and second systems; and calculating a probability of hydrogen molecules moving to a random open binding site on the metalloborane, wherein the probability correlates to the hydrogen storage capacity of the metalloborane. In this embodiment the two-system model may comprise hydrogen in a gas phase as a first system and hydrogen absorbed to the metalloborane as the second system. Also, the metalloborane may be $M_2B_6H_6$ wherein M is a transition metal. Particularly, the transition metal is titanium or scandium. In addition, the metal organic framework may be an MOF5 comprising $M_2B_6H_6$—$(COOH)_2$. Particularly, the metal organic framework is an MOF5 comprising $Ti_2B_6H_6$—$(COOH)_2$ or is an MOF5 comprising $Sc_2B_6H_6$—$(COOH)_2$.

In order to overcome the deficiencies in the prior art and to achieve the objectives and advantages set forth above and below, provided herein are compounds, compositions, systems and methods for storage of hydrogen gas. Particularly, metalloboranes are useful as a material for high-density hydrogen storage.

An advantage of the present invention is the utilization of boron in metalloboranes. Boron is unique in its bonding characteristics and is one of the few compounds that are able to establish a three-center bonding scheme as well as being able to mimic the bonding structure of carbon. Although boron in a six-member benzene-type ring configuration is unstable due to electron deficiency of boron in this configuration, the electronic structure can be stabilized via one of the two mechanisms; (i) the molecule can reconfigure its structure, making use of three center two-electron bonding; or (ii) it can acquire electrons from surrounding environment, depending on the specifics of the environment such as the electron affinities of the surrounding atoms.

Metalloboranes are transition metal and borane compounds that obey a novel-bonding scheme. The transition metal atoms is found herein to be able to bind up to 10 $H_2$-molecules with an average binding energy of 30 kJ/mole of $H_2$, which lies favorably within the reversible adsorption range. The —$B_6H_6$ is in planar form is more stable than the competing closo-$B_6H_6$ form. Among the first row transition metal atoms, Sc and Ti are found to be the optimum in maximizing the $H_2$ storage on the metalloborane cluster. Additionally, being ionically bonded to the borane molecule, the transition metals do not suffer from the aggregation problem, which has been the biggest hurdle for the success of transition metal-decorated graphitic materials for hydrogen storage. The gravimetric density of hydrogen absorbed and stored by this molecule is up to 13% wt/wt.

Another advantage of the present invention is the inclusion of a metal organic framework to absorb hydrogen. The metal organic framework comprises organic crystalline compounds consisting of metal ion complexes coordinated to rigid or semi-rigid organic "linker" molecules that can form highly open and porous one to three dimensional structures. The pores, which can be very large and stable, may be used for storage of gases. There are a multitude of choices for the metal ions and linker molecules leading to a huge variety of crystal structures and physical properties. The organic linkers and inorganic joints can be designed. These choices of metal ions affect significantly the ability of the metal organic framework to absorb hydrogen efficiently.

Thus, the present invention provides molecular hydrogen storage compounds or compositions. A titanium or scandium metalloborane compound absorbs hydrogen or is embedded into or linked to a Metal Organic Framework to form a hydrogen storage composition to improve hydrogen storage. Since the borane 6-atom ring has identical bonding properties as carbon rings, it is possible to link the metalloboranes into metal organic frameworks, which are thus able to adsorb hydrogen via Kubas interaction as well as the well-known van der Waals interaction. More specifically, the Metal Organic Framework used herein is MOF5 ($Zn_4O$ $(BDC)_3$, where $BDC^{2-}$=1,4-benzenedicarboxylate), where the linear 1,4-benzenedicarboxylate struts are modified to $M_2B_6H_6$-dicarboxylate struts to form a cubic network. For example, the titanium metalloboranes in a MOF5 structure are predicted to be able to absorb up to 11.5% hydrogen per weight at 100 bar of pressure, which is a significant improvement over the current industrial method for hydrogen storage.

As such, the present invention provides hydrogen storage systems or compositions in which molecular hydrogen or hydrogen gas is absorbed to the metalloborane in the compound or the MOF-metalloborane composition. The structural configuration of the stored hydrogen is $M_2B_6H_6$-(n,m)$H_2$ or MOF5-$M_2B_6H_6$-(n,m)$H_2$ where n and m independently are 0 to 6.

The present invention also provides methods to absorb and store hydrogen gas. The gas is passed or flowed over the metalloborane or through the MOF5-metalloborane material in ambient pressure and temperature. The density of the hydrogen gas is about 12% wt/wt based on the weight of the metalloborane or MOF5-metalloborane. Particularly, titanium or scandium is used in the metalloborane. Moreover, it is contemplated that the stored hydrogen can be released to fuel or power a vehicle.

Also provided are methods for calculating the hydrogen storage capacity of a metalloborane, for example, in silico, based on the crystal structure of a synthesized metal organic framework-metalloborane. Lattice data of the crystal is input into an algorithm for calculating and predicting the total hydrogen uptake for the titanium Metelloborane-MOF5 system. The algorithm is a modified Metropolis Monte-Carlo algorithm. Specifically, a two-system model is used with hydrogen in the gas phase as the first system and hydrogen absorb to the Titanium metalloborane as the second system. Metropolis Monte-Carlo algorithms is used to sample the thermodynamic state of the systems. The algorithm is able to predict that the Metalloborane-MOF5 is about to store up to 11.5% per weight of hydrogen at 100 bars.

The following example(s) are given for the purpose of illustrating various embodiments of the invention and are not meant to limit the present invention in any fashion.

Example 1

Methodology

The calculating methods used in the present invention are first-principles density-functional theory (DFT) calculations with the generalized gradient approximation (GGA) and Vanderbilt ultrasoft pseudopotentials with Perdew Wang (PW91) exchange-correlation functional, as implemented in the Quantum Espresso ab initio simulation package and the FreeON Gaussian based code suite for structural studies using the Becke-Lee-Yang-Parr Hybrid Functional. For Quantum Espresso, a plane wave cut off of 50 Ry was used to obtain convergence of the ground state total energy. In all energy calculations the molecule was placed in a large box with a side length of 20 Å to avoid interaction by its images. Structural relaxation of atomic positions was carried out until the residual forces were less than 0.02 eV/A. Gamma point total energy calculations are carried out throughout the study.

Example 2

Figure 1A:
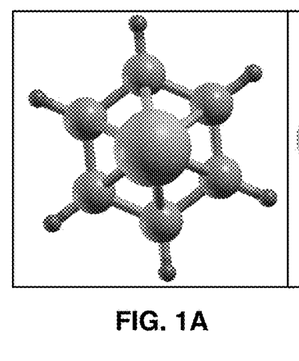
FIG. 1A is the top view of the molecular structure of a planar $M_2B_6H_6$ (M=Al, Sc, Ti).
Figure 1B:
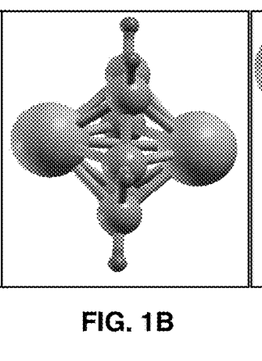
FIG. 1B is the side view of the molecular structure of a planar $M_2B_6H_6$ (M=Al, Sc, Ti).
Figure 1C:
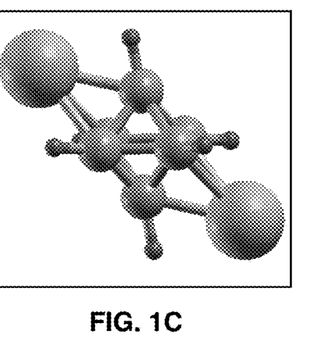
FIG. 1C is the closo-structure of a planar $M_2B_6H_6$ (M=Al, Sc, Ti).
Figure 2:
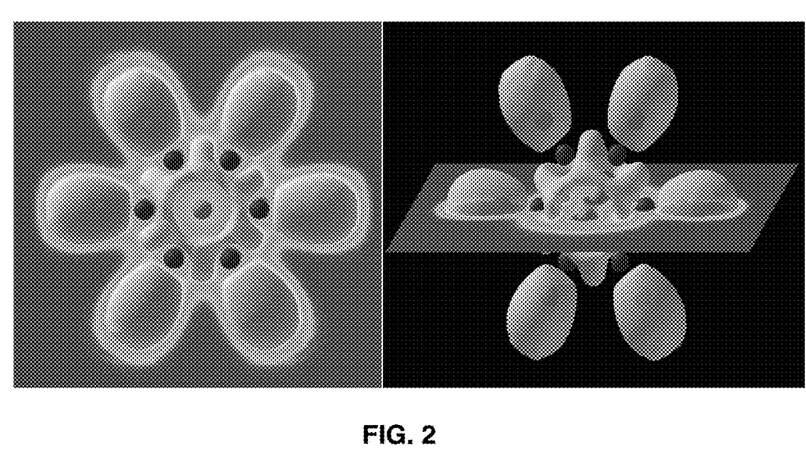
FIG. 2 illustrates the electronic isosurface of $Sc_2B_6H_6$ computed in Quantum Espresso. The six-boron ring has a well formed Pi-orbital above and below the boron ring. Also noteworthy is lack of electron density around the metal cations.

Metalloboranes $B_6H_6$ has two different structures, the closo- and the planar. FIGS. 1A-1B show the relaxed geometry for $Sc_2B_6H_6$ from two different views, and FIG. 1C shows the competing structure closo-$Sc_2B_6H_6$. Without the presence of the cations, the closo-structure has the lowest energy. However, in the presence of cations the planar structures can be the lowest in energy. The energy of planar—$Sc_2B_6H_6$ is calculated to be lower than closo counterpart by 1.3 eV. The energy of planar—$Ti_2B_6H_6$ is calculated to be lower than closo-$Ti_2B_6H_6$ by 2.4 eV. FIG. 2 illustrates the constant electron density iso-surface for $Sc_2B_6H_6$. It is evident that the boron-boron bonds are formed on the basis of the π-orbital aromatic bonds, as has been previously explored. It is also noticeable that electron density around the metal cations is relatively low.

Tables I and II show calculated the bond lengths, binding energies and partial charges for the planar and closo-$M_2B_6H_6$ molecular species for M=Al, Sc and Ti. Table III shows ionization energies for metal atoms Al, Sc and Ti.

The results indicate that $Ti_2B_6H_6$ is the most stable. This can be partially explained based on ionization energies (IE) of Al, Sc, and Ti and the degree of charge transfer of the metal ions. As discussed above, the relative stability of the metalized boron hydrides depends on the relative energies of charge transfer. It is known that Al has larger $2^{nd}$ and $3^{rd}$ ionization energies than Sc and Ti. Therefore it is more difficult for Al to yield its electron(s) to the ring. To further explore this, the relative charges on each atom in the $M_2B_6H_6$ as well as amount of charge transferred by the metal atom in both the planar and closo-$M_2B_6H_6$ configurations are calculated, respectively.

As shown in Table II, Al has the lowest charge transfer in both planar and closo-structures and the longest boron-boron bond length while Ti has the largest charge transfer in both planar and closo-structures and the shortest boron-boron bond length. Therefore, $Ti_2B_6H_6$ has the most stable structure and $Al_2B_6H_6$ has most unstable structure.

TABLE I

Bond lengths (Angstroms) and formation energies of different species of $M_2B_6H_6$ in the planar and closo configurations (M = Al, Sc, Ti)

| Species | Formation Energy (eV) | Gap (eV) | Bond Lengths | | |
|---|---|---|---|---|---|
| | | | B—H (A) | B—M (A) | B—B (A) |
| closo-$Al_2B_6H_6$ | −17349.992036 | 4.109 | 1.191 | 2.411 | 1.733 |
| planer-$Al_2B_6H_6$ | −17346.654335 | 1.423 | 1.177 | 2.155 | 1.766 |
| closo-$Sc_2B_6H_6$ | −45550.902078 | 1.524 | 1.194 | 2.496 | 1.740 |
| planer-$Sc_2B_6H_6$ | −45551.660772 | 2.476 | 1.191 | 2.378 | 1.711 |
| closo-$Ti_2B_6H_6$ | −50376.955179 | 1.094 | 1.201 | 2.284 | 1.733 |
| planer-$Ti_2B_6H_6$ | −50379.718612 | 1.967 | 1.189 | 2.249 | 1.695 |

TABLE II

Partial charges on the different species of $M_2B_6H_6$ in the planar and closo configurations (M = Al, Sc, Ti)

| Species | Charge M | Charge B | Charge H |
|---|---|---|---|
| closo-$Al_2B_6H_6$ | 1.075 | −0.325 | −0.032 |
| planer-$Al_2B_6H_6$ | 2.387 | −0.787 | −0.008 |
| closo-$Sc_2B_6H_6$ | 1.138 | −0.345 | −0.033 |
| planer-$Sc_2B_6H_6$ | 2.499 | −0.820 | −0.012 |
| closo-$Ti_2B_6H_6$ | 1.789 | −0.559 | −0.037 |
| planer-$Ti_2B_6H_6$ | 2.663 | −0.855 | −0.032 |

TABLE III

Ionization Energies from Reference

| Species | 1$^{st}$ Ionization (eV) | 2$^{nd}$ Ionization (eV) | 3$^{rd}$ Ionization (eV) |
|---|---|---|---|
| Aluminum | 0.598 | 1.882 | 2.844 |
| Scandium | 0.656 | 1.279 | 2.475 |
| Titanium | 0.683 | 1.357 | 2.748 |

Example 3

Hydrogen Absorption

Tables IV and V shows the calculated binding energies for hydrogen absorbed onto the $Sc_2B_6H_6$ and $Ti_2H_6B_6$ metalloboranes. The binding energy is defined as the energy needed to remove an excess hydrogen molecule. The zero point energy of hydrogen is also calculate and corrected, $$E_{BE} = \begin{cases} E(n, n) - E(n, n-1) + \frac{3}{2}\hbar\omega_0 \\ E(n, n+1) - E(n, n) + \frac{3}{2}\hbar\omega_0 \end{cases} \quad \text{(Eq. 1)}$$

wherein $E_{BE}$ is binding energy, E(n,n) is energy of hydrogen molecule configuration, hbar times $\omega_0$ is Planck's constant times the natural oscillation frequency of hydrogen or zero point energy.

All of the binding energies for $Sc_2B_6H_6$ and $Ti_2H_6B_6$ listed in Tables IV and V are in the 5 kJ/mole to 25 kJ/mole (including zero point energy) range, which is thermodynamically ideal for efficient hydrogen absorption and release, thus, ideal for hydrogen storage.

TABLE IV

Binding Energies for $Sc_2B_6H_6$ + (n,m)$H_2$

| Number of Hydrogen | Hydrogen Configuration | Binding Energy (kJ/mole) |
|---|---|---|
| 1 | (0,0)→(0,1) | 30.021 |
| 2 | (0,1)→(1,1) | 35.056 |
| 3 | (1,1)→(1,2) | 21.716 |
| 4 | (1,2)→(2,2) | 34.066 |
| 5 | (2,2)→(2,3) | 30.187 |
| 6 | (2,3)→(3,3) | 37.846 |
| 7 | (3,3)→(3,4) | 13.627 |
| 8 | (3,4)→(4,4) | 14.335 |

TABLE V

Binding Energies for $Ti_2B_6H_6 + (n,m)H_2$

| Number of Hydrogen | Hydrogen Configuration | Zero Point Energy of $H_2$ (kJ/mole) | Binding Energy (kJ/mole) |
|---|---|---|---|
| 1 | (0,0)→(0,1) | 4.2247 | 25.7909 |
| 2 | (0,1)→(1,1) | 4.2413 | 23.4463 |
| 3 | (1,1)→(1,2) | 4.2524 | 26.1210 |
| 4 | (1,2)→(2,2) | 4.2672 | 28.7958 |
| 5 | (2,2)→(2,3) | 4.2773 | 23.1855 |
| 6 | (2,3)→(3,3) | 4.2792 | 22.7275 |
| 7 | (3,3)→(3,4) | 4.2959 | 20.1329 |
| 8 | (3,4)→(4,4) | 4.3110 | 22.0124 |
| 9 | (4,4)→(4,5) | 4.4015 | 17.8944 |
| 10 | (4,5)→(5,5) | 4.5003 | 17.7529 |

Figure 3:
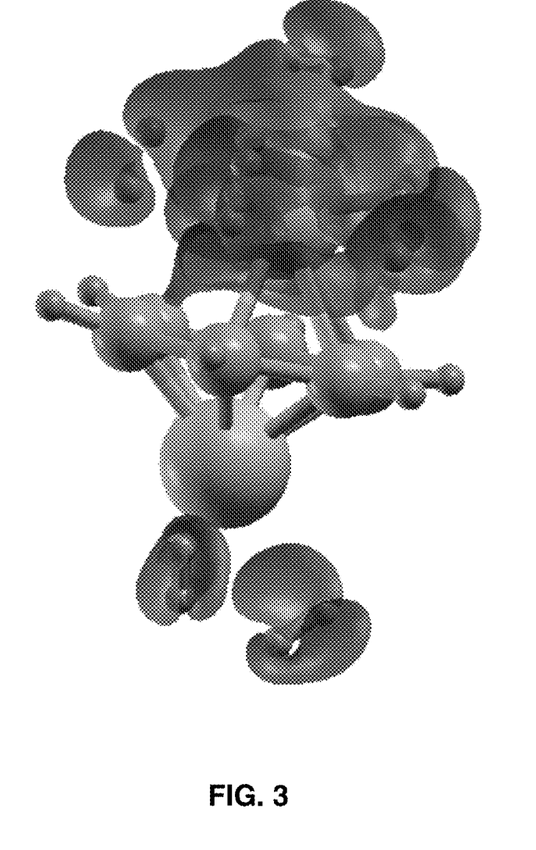
FIG. 3 illustrates isosurface bonding charge density in $Sc_2B_6H_6$-$(6,2)H_2$ configuration. This configuration refers to hydrated $Sc_2B_6H_6$ with 8 $H_2$ molecules attached to $S_c$ on both sides of $Sc_2B_6H_6$. Charge accumulations and depletion between Sc and $H_2$ molecules. The H—H bond length is elongated from 0.74 A to 0.80 A due to Kubas interaction.

FIG. 3 shows the differential isosurface plot of the bonding charge density in $Sc_2B_6H_6$-(6,2)$H_2$ configuration. This configuration refers to the hydrated $Sc_2B_6H_6$ with 8 $H_2$ molecules attached to Sc on both sides of $Sc_2B_6H_6$. Charge accumulations and depletion are shown between Sc and $H_2$ molecules. The H—H bond length is elongated from 0.74 Angstroms to 0.80 Angstroms due to the Kubas interaction as the boding is d-shell in character, which corresponds to the Kubas mechanism. The results also indicate that approximately 0.1 electrons are involved in the Kubas bond, which complies the theoretical magnitude of the Kubas binding energy.

Figure 4A:
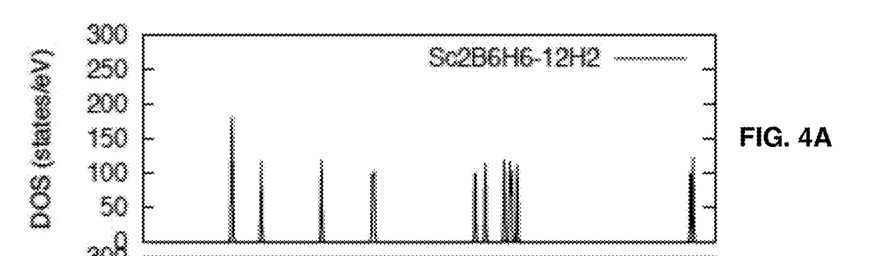
Figure 4B:
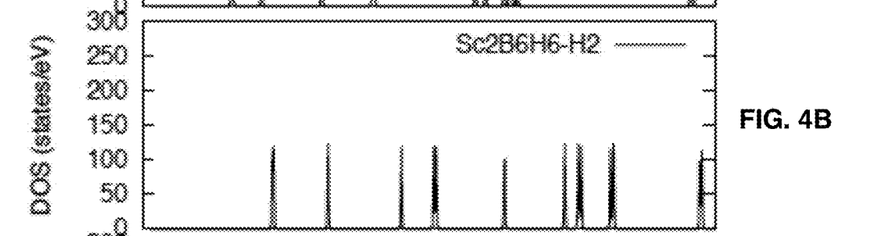
Figure 4C:
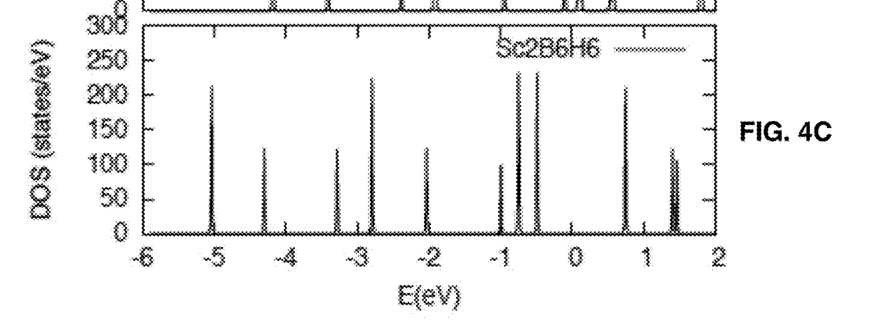
FIG. 4C shows the density of states for $Sc_2B_6H_6$-$(6,6)H_2$. Due to Kubas interaction between s orbitals of $H_2$ and the d-orbitals of Sc, d orbitals are pushed down below the Fermi level as $H_2$ is absorbed to the molecule.

To further illustrates the Kubas mechanism, FIGS. 4A-4C shows the change in the density of state (DOS) for $Sc_2B_6H_6$ as the molecule absorbs hydrogen. As shown in the FIGS. 4A-4C, the d-orbitals, which were originally above the Fermi energy (zero) are pushed down below the Fermi level as $H_2$ is absorbed to the molecule. Due to large charge transfer on titanium cation and the depopulation of the p-orbitals, these compounds do not suffer from the titanium aggragation or the hydrogen dissociation problem from which titanium decorated graphite materials suffer.

Example 4

Metal Organic Framework

Figure 5:
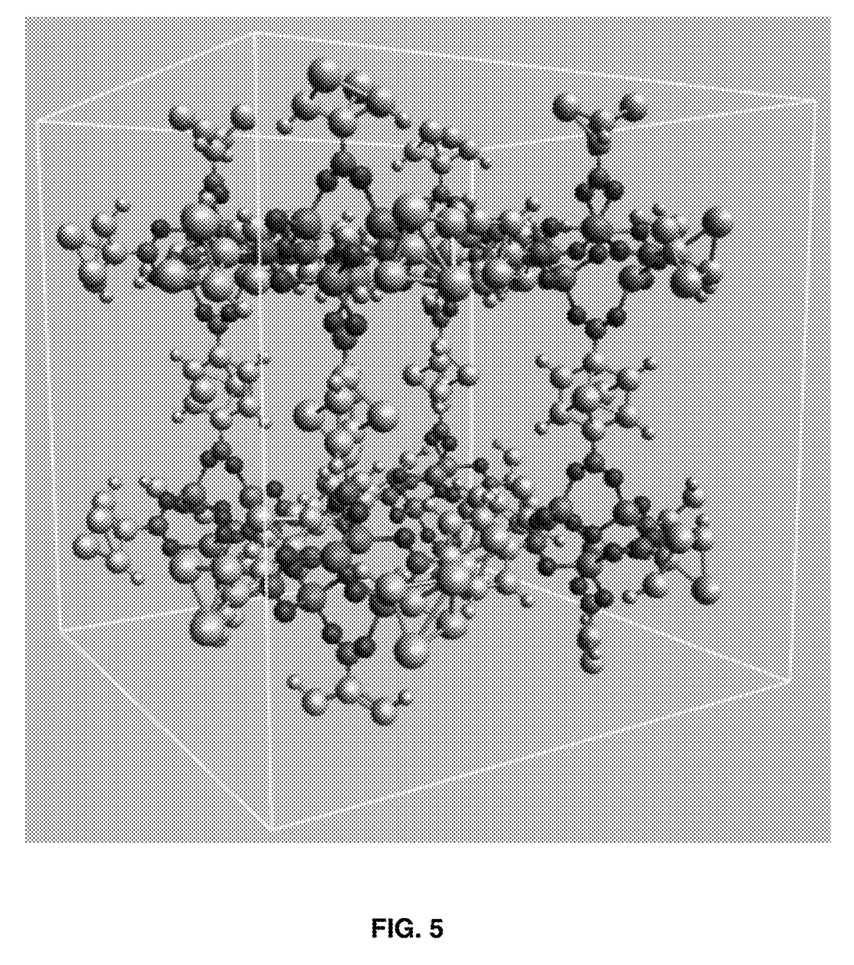
FIG. 5 illustrates the molecular structure of $Ti_2B_6H_4(COOH)_2$ in a metal organic framework (MOF5). The addition of the titanium to the MOF5 significantly increase hydrogen uptake at 300K.

FIG. 5 illustrates the crystal structure of a Molecular Organic Framework (MOF), specifically a MOF5 crystal. The Terephthalic acid linker molecules benzene ring is replaced with the $Ti_2B_6H_6$ molecule. The calculation results indicate this crystal structure has a lattice constant of 25.7 Angstroms. Excluded volume due to the molecular structure is calculated to be approximately 20% of the total volume. The structure in FIG. 5 is used as a model for the chemical absorption for the calculation of the hydrogen uptake in the present invention.

Example 5

Synthesis of MOF5-$Ti_2B_6H_6$

Figure 6A:
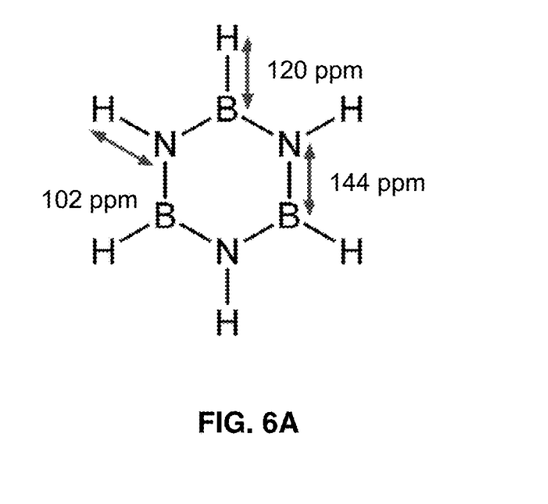
FIGS. 6A-6B show the chemical structure of borazine (FIG. 6A) and borazine-1,3,5-tetracarboxylic acid (FIG. 6B).

Borazine or inorganic benzene is used to synthesize the MOF-$Ti_2B_6H_4(COOH)_2$ (1) in three main steps. Borazine (FIG. 6A) is an inorganic compound with the chemical formula $B_3N_3H_6$. The compound is isoelectronic and isostructural with benzene. Like benzene, borazine is a colorless liquid.

Figure 6B:
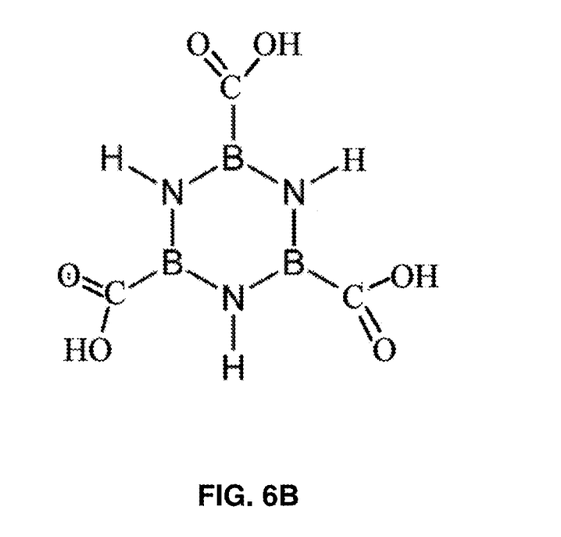

In the first step the borazine is functionalized by a two sub-reactions process to form borazine-1,3-dicarboxylic acid, $B_3N_3H_4(COOH)_2$. The first sub-reaction methanates the 1 and 3 boron atoms using a modified UOP-isomar process (2). This process can be modified to efficiently methanate the 1 and 3 Boron atoms selectively, producing 1,3,5 tetramethylborazine, $B_3N_3H(CH_3)_3$. The second sub-reaction converts the methyl-groups into borazine-1,3,5-tricarboxylic acid (FIG. 6B) via a cobalt-manganese catalyst (3). The borazine-1,3-5-tetracarboxylic acid is utilized as a linker molecule in the MOF structure.

In the second step, the borazine in the borazine-1,3,5-tetracarboxylic acid linker is converted into the metalloborazine molecule. The N—H subunits in the linker molecule are replaced with B—N subunits via the following reaction in which the metal is titanium:

$$B_3N_3H_3(COOH)_3 + 3Ti(BH_4) \rightarrow Ti_2B_6H_3(COOH)_3 + Ti(N\ H_2)_3 + 3H_2.$$

Example 6

Hydrogen Uptake in Metal Organic Framework

The total hydrogen uptake for the Titanium Metelloborane-MOF5 system is calculated using a modified Metropolis Monte-Carlo algorithm based on results of hydrogen binding to Titanium Metalloboranes from literature. A two-system model, with hydrogen in the gas phase as the first system and hydrogen absorbed to the Titanium Metalloborane as the second system, is constructed. Metropolis Monte-Carlo algorithms are used to sample the thermodynamic state for the systems. The equation of state developed by Lemmon et al. is used for hydrogen in gas phase. The equation allows direct access to the gas pressure of the system as the simulation progresses. The state of the hydrogen gas is represented by first defining the compressibility factor, $$Z(n, P, T) = \frac{PV^*}{nkT} = 1 + \sum_{i=1}^{9} a_i \left(\frac{100K}{T}\right)^{b_i} \left(\frac{P}{1000\ \text{bars}}\right)^{c_i} \quad \text{(Eq. 2)}$$

Where Z is compressibility factor, P is pressure, n is the number of moles, T is temperature, k is Boltzmann's constant and V* is the total volume minus the excluded volume due to the crystal structure of MOF5. The V' for Titanium metalloborane-MOF5 structure is calculated to be 81% of the total volume. In the simulation process, $Ti_2B_6H_6$-MOF5 structure is divided into unit cells.

As illustrated in FIG. 5, there are 48 titanium atoms that have 240 binding sites in one unit cell. The binding energy per titanium atom is calculated and presented in Table IV. Zero point motion is included within the calculation of the Binding Energies.

In the calculation process, the number of hydrogen molecules in the simulation is first specified and each hydrogen molecule is randomly placed at one of the 240 binding sites. Then a hydrogen molecule is randomly chosen for the calculation. If the chosen hydrogen molecule is in the gas phase, the probability of the hydrogen molecule transferring to a random open binding site is calculated. If the molecule is in the binding phase, the probability of the chosen molecule transitioning to the gas phase is calculated. The equations to calculate the probabilities are, $$P[i \rightarrow f] = \max[1, \text{Exp}[-\Delta E/kT]] \quad \text{(Eq. 3)}$$

where $$E_{abs}(n, T) = \frac{3}{2}nkT + \sum_{i=1}^{n} E_{BE}^{i} \quad \text{(Eq. 4)}$$

$$E_{gas}(n, P, T) = \frac{5}{2}nkT\, Z(n, P, T)$$

and

$$\Delta E = \begin{cases} (E_{abs}(n-1, T) + E_{gas}(n+1, P^*, T)) - \\ \quad (E_{abs}(n, T) + E_{gas}(n, P, T)) & \text{absorbate} \to \text{gas} \\ (E_{abs}(n+1, T) + E_{gas}(n-1, P^*, T)) - \\ \quad (E_{abs}(n, T) + E_{gas}(n, P, T)) & \text{gas} \to \text{absorbate} \end{cases}$$

where $E_{abs}$ is absorbate energy, $E_{gas}$ is gas energy

Figure 7:
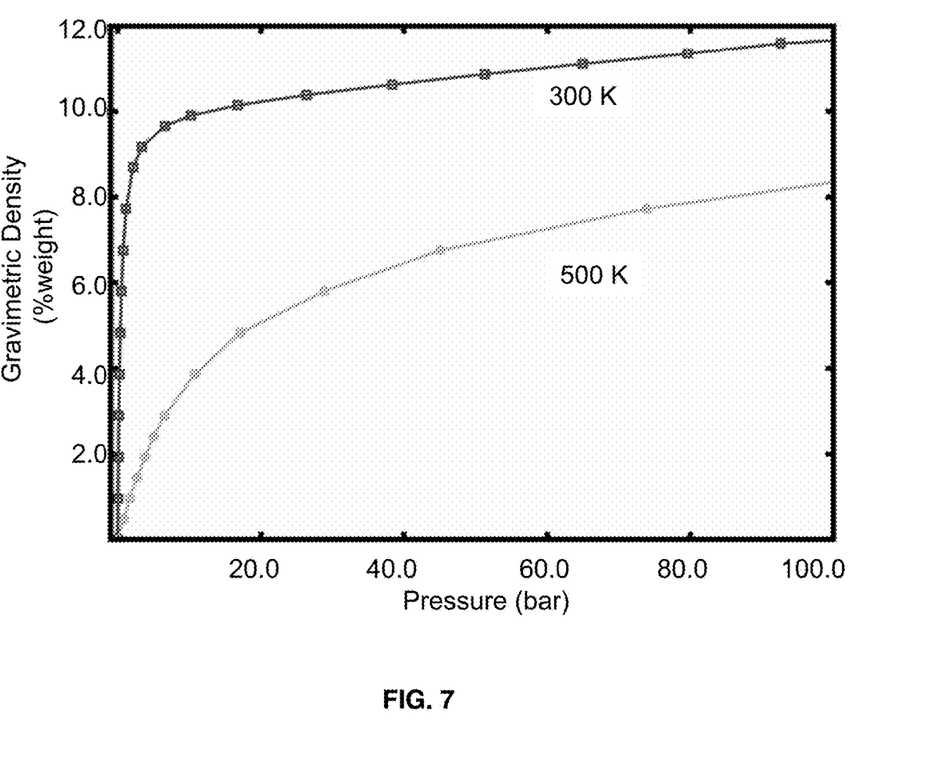
FIG. 7 shows an absorption vs. pressure curve for MOF5-$Ti_2B_6H_4(COOH)_2$ system computed based on the Hydrogen Binding energies in Table V using a Monte Carlo algorithm. The curve with square points is computed at 300K (room temperature) and the curve with sphere points is computed at 500K (auto exhaust temperature).

In this simulation the pressure is obtained from the gas Equation and averaged over ten million instances. FIG. 7 shows the hydrogen density-pressure curve of the simulated system for the temperatures 300 Kelvin and 500 Kelvin. These results indicate that the Titanium Metalloborane-MOF5 is able to store hydrogen up to 11.5% per weight at 100 bar.

What is claimed is:

1. A metalloborane compound linked to a metal organic framework 5 (MOF5) having a chemical structure:

wherein M is a transition metal.

2. The metalloborane compound of claim 1, wherein the structure is MOF5-$Ti_2B_6H_6$—(COOH) or MOF5-$Sc_2B_6H_6$—(COOH).

3. A method for storing hydrogen, comprising the step of:
flowing hydrogen gas to contact the metalloborane of claim 1 whereby hydrogen molecules bind thereto.

4. The method of claim 3, wherein the stored hydrogen comprises a structural configuration of $M_2B_6H_6$-(n,m)$H_2$ wherein n and m are independently 0 to 6.

5. The method of claim 4, wherein M is titanium or scandium.

6. The method of claim 3, further comprising releasing the stored hydrogen to power a vehicle.

7. A molecular hydrogen storage system, comprising:
the metalloborane compound of claim 1; and
one or more hydrogens absorbed to the metalloborane.

8. The molecular hydrogen storage system of claim 7, wherein said hydrogen is absorbed via Kubas interaction and van der Waals interaction.

9. The molecular hydrogen storage system of claim 7, having a structural configuration of $M_2B_6H_6$-(n,m)$H_2$ configuration wherein n and m are independently 0 to 6.

10. A hydrogen storage composition, comprising MOF5-$Ti_2B_6H_6$—(COOH)$_2$ or MOF5-$Sc_2B_6H_6$—(COOH)$_2$.

11. A method for storing hydrogen, comprising the step of:
flowing hydrogen gas for absorptive contact with the hydrogen storage composition of claim 10 whereby hydrogen molecules bind to the $Ti_2B_6H_6$ or $Sc_2B_6H_6$ in a structural configuration $Ti_2B_6H_6$-(n,m)$H_2$ or $Sc_2B_6H_6$-(n,m)$H_2$ within the hydrogen storage composition; wherein n and m are independently 0 to 6.

12. The method of claim 11, further comprising releasing the stored hydrogen to power a vehicle.

13. A molecular hydrogen storage system, comprising:
the hydrogen storage composition of claim 10; and
one or more hydrogens absorbed to the $Ti_2B_6H_6$ or $Sc_2B_6H_6$ in a structural configuration $Ti_2B_6H_6$-(n,m)$H_2$ or $Sc_2B_6H_6$-(n,m)$H_2$ within the hydrogen storage composition; wherein n and m are independently 0 to 6.

14. The molecular hydrogen storage system of claim 13, wherein said hydrogen is absorbed via Kubas interaction and van der Waals interaction.

15. A method for calculating the hydrogen storage capacity of a metalloborane, comprising the steps of:
synthesizing a metal organic framework-metalloborane crystal structure;
calculating lattice data for the crystal structure;
inputting the lattice data into a two-system model of hydrogen;
sampling the thermodynamic states of the first and second systems; and
calculating a probability of hydrogen molecules moving to a random open binding site on the metalloborane, wherein the probability correlates to the hydrogen storage capacity of the metalloborane.

16. The method of claim 15, wherein the two-system model comprises hydrogen in a gas phase as a first system and hydrogen absorbed to the metalloborane as the second system.

17. The method of claim 15, wherein the metalloborane is $M_2B_6H_6$ wherein M is a transition metal.

18. The method of claim 17, wherein the transition metal is titanium or scandium.

19. The method of claim 15, wherein the metal organic framework is an MOF5 comprising $M_2B_6H_6$—(COOH)$_2$, $Ti_2B_6H_6$—(COOH)$_2$, or $Sc_2B_6H_6$—(COOH)$_2$.

* * * * *